United States Patent [19]
Avison et al.

[11] Patent Number: 5,166,450
[45] Date of Patent: Nov. 24, 1992

[54] PRODUCTION OF HYDROXYKETONES

[75] Inventors: Carl A. Avison, Hull; Ian D. Dobson, North Humberside; Benjamin P. Gracey, North Humberside; Barry Hudson, North Humberside; Thakor Kikabhai, North Humberside, all of England

[73] Assignee: BP Chemicals Limited, London, England

[21] Appl. No.: 771,753

[22] Filed: Oct. 4, 1991

[30] Foreign Application Priority Data

Oct. 10, 1990 [GB] United Kingdom ............... 90022071

[51] Int. Cl.⁵ ............................................. C07C 45/75
[52] U.S. Cl. ................................... 568/388; 568/343; 568/312
[58] Field of Search .................... 568/388, 343, 312

[56] References Cited

U.S. PATENT DOCUMENTS

| | | | |
|---|---|---|---|
| 2,760,983 | 8/1956 | MacLean et al. | 568/388 |
| 4,301,310 | 11/1981 | Wagner | 568/388 |
| 4,326,086 | 4/1982 | Mohring et al. | 568/388 |
| 4,358,019 | 11/1982 | Stemmler et al. | 568/388 |
| 4,782,186 | 11/1988 | Beevor | 568/388 |

FOREIGN PATENT DOCUMENTS

| | | | |
|---|---|---|---|
| 547098 | 5/1986 | European Pat. Off. | 568/388 |
| 59-164745 | 9/1984 | Japan | 568/388 |
| 59-164746 | 9/1984 | Japan | 568/388 |
| 60-184038 | 9/1985 | Japan | 568/388 |

*Primary Examiner*—James H. Reamer
*Attorney, Agent, or Firm*—Brooks Haidt Haffner & Delahunty

[57] ABSTRACT

This invention relates to an improved process for the production of hydroxyketones, especially dihydroxyacetone, by the condensation of one or more aldehydes in the presence of a catalyst and the use of specific process train. The product of this process is a relatively pure and any waste products from the reaction are environmentally friendly because none of the chemical components are discharged into the waste streams.

15 Claims, 1 Drawing Sheet

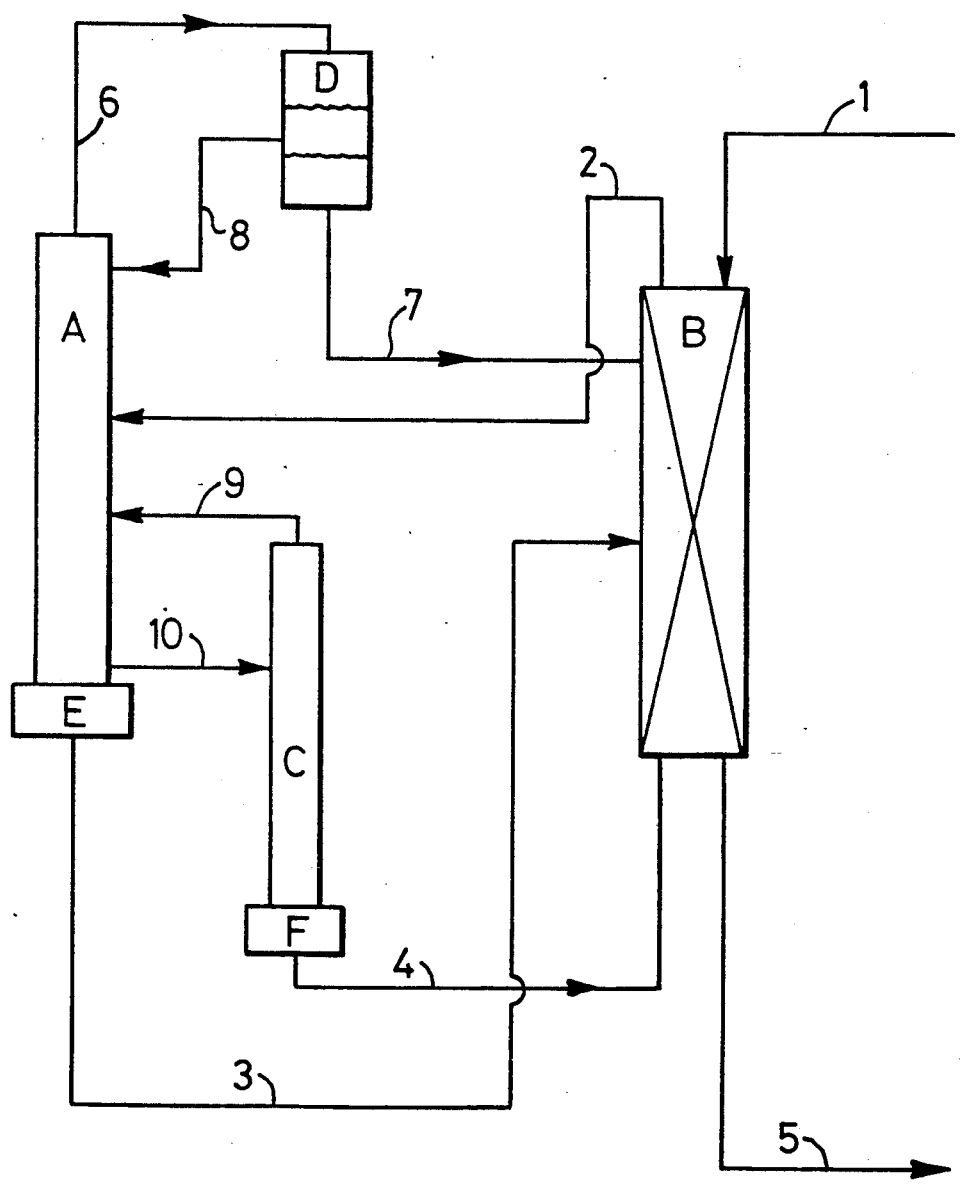

PRODUCTION OF HYDROXYKETONES

This invention relates to an improved process for the production of hydroxyketones, especially dihydroxyacetone, by the condensation of one or more aldehydes in the presence of a catalyst.

Dihydroxyacetone (hereafter "DHA") is a valuable raw material for the production of alcohols and esters, especially glycerol which in turn is used to produce various esters, printing inks, foodstuffs, in toothpastes, in antifreezes, as a moistening agent in tabacco, in soaps and for producing nitroglycerine.

Our published EP-A-306215 describes a process for synthesising glycerol by initially self-condensing formaldehyde in a substantially anhydrous state to DHA followed by hydrogenation of the DHA. In this document, and in other prior published documents on self-condensation reaction such as the article by Matsumoto, T et al in J A C S, 1984 106, pp 4289–4832 and in EP-A-245976, the self-condensation stage has been carried out in the presence of a base such as triethylamine and halide ions such as bromide ions. The bromide ions come from the salt of the heterocyclic catalyst such as the thiazolium bromide. However, these processes have been commercially unattractive because the catalyst used is known to be deactivated in the presence of water—a by-product of the process. Moreover, a relatively laborious process of drying the reactants such as formaldehyde is necessary before use.

It has now been found that by designing a combination of a condensation reactor and an extractor the above problems can be mitigated.

Accordingly, the present invention is a continuous process for producing hydroxyketones by condensation of one or more aldehydes in the presence of a catalyst characterised in that the process is carried out in a process train comprising at least two columns A and B such that:

1. column A is the condensation reactor which is provided with notional zones comprising:
   a. a middle zone into which is fed a feed comprising the aldehyde(s), a solvent stream comprising at least one water-immiscible organic solvent, and a catalyst;
   b. a bottom zone in which a condensation of the aldehyde(s) occurs under substantially anhydrous conditions and from which a solution comprising the hydroxyketone, catalyst and the solvent stream is withdrawn for extraction of the hydroxyketone product therefrom in column B; and
   c. an upper zone from which a mixture comprising unreacted aldehyde(s), whether as such or in bound form, one or more components of the solvent stream, whether or not water-miscible, and water are withdrawn, and 2. column B is an extraction column which is provided with three notional zones comprising:
   a. a middle zone into which is fed the solution comprising the hydroxyketone, the catalyst and the solvent stream withdrawn from the bottom of column A;
   b. a bottom zone
      (i) into which is fed a solvent stream comprising the water-immiscible organic solvent and
      (ii) from which an aqueous solution of the hydroxyketone product is withdrawn; and
   c. an upper zone
      (i) into which is fed an aqueous solution of the aldehyde(s) and
      (ii) from which a feed comprising the solvent stream, the aldehyde(s), whether as such or in bound form, and catalyst is withdrawn for recycle to the middle zone of column A, thereby enabling in column B a simultaneous recovery of the hydroxyketone product and recycle of the catalyst to column A.

By "water-immiscible" is meant here and throughout the specification that said organic solvent is only partially soluble in water and the solubility of the solvent is not greater than 50% w/w at the operating temperature of column B.

By "substantially anhydrous conditions" as used herein and throughout the specification is meant that the water content of the reaction mixture in this zone is less than 0.4% w/w. The water content is preferably below 0.1% w/w of the reaction mixture in this zone.

The process of the present invention can be operated either for self-condensation of an aldehyde or for the cross-condensation of dissimilar aldehydes. For the sake of clarity and ease of understanding the inventive concepts in the present invention, the following description will describe in detail the self-condensation of formaldehyde as an illustration.

A feature of this process is that the operation of columns A and B can be readily adjusted and adapted to various solvents and column conditions. The number of plates in these columns, the temperature profile of the column and the column pressures used to operate these columns will depend upon several factors including the nature of the solvent stream, the amount of water in the formaldehyde employed and the nature of the catalyst used in these columns.

Thus for a column in which the aldehyde used is formaldehyde, suitably as commercial formalin (comprising 30%–60% w/w formaldehyde, remainder water and traces of methanol), the water-immiscible component of the solvent stream used suitably comprises a hydrocarbon, a halohydrocarbon, an ether, an ester or an alcohol, preferably aliphatic alcohols and is most preferably one or more of e.g. secondary butanol, isobutanol, iso-amyl alcohol, active amyl alcohols and 4-methylpentan-2-ol.

The catalyst is suitably derived from a thiazolium or an imidazolium salt such as e.g. an alkyl benzothiazolium halide. The object is to pretreat the salt in such a manner that the anion $X^-$ in the salt, which in this case will be a halide ion, is removed from the salt as $H^+X^-$. The removal of $H^+X^-$ can be achieved by passing a solution of a salt through e.g. an appropriate ion-exchange resin column. Whilst the removal of the anions is not essential for the success of the condensation reaction, it is nevertheless beneficial to remove such anions as $H^+X^-$ because the presence of such ions may:

a) give rise to corrosion of equipment used;
b) poison any catalysts used during any subsequent reaction of the self-condensation product such as e.g. hydrogenation; and/or
c) result in the formation of undesirable by-products such as e.g. formals.

Thus column A in which the self-condensation reaction occurs suitably has about 10 to 40 theoretical plates. The notional middle zone of a 40-plate column can be defined by the region between theoretical plates 15 and 30. The bottom zone of this column can be defined as the region below theoretical plate 15 and the upper zone can be defined as the region above theoretical plate 30.

In this case, a feed comprising formaldehyde, the solvent stream comprising the water-immiscible solvent and the catalyst derived from a benzothiazolium halide, is fed into the middle zone of column A at about theoretical plate 20. The self-condensation can be carried out in this column and a vapour stream is withdrawn overhead. If the water-immiscible component of the solvent stream is an alcohol, the aldehyde in the overhead vapour stream may be in a bound form such as e.g. a hemiformal or a hemiacetal. This overhead vapour can be advantageously fed, after condensation, into a decanter in which the condensates may, depending upon the presence of any water-immiscible solvents therein, separate into an aqueous phase (containing any water-miscible solvents, water and formaldehyde) and an organic phase (containing the water-immiscible solvent, formaldehyde and small quantities of water). The organic phase can be recycled to the top of column A where the water-immiscible solvent and formaldehyde act as a medium which force the reactants back into the middle zone and prevent unnecessary vapourisation and hence loss of the reactant formaldehyde and solvent stream into the overheads. The aqueous layer can be recycled back to column B the function of which is explained in greater detail below.

In the case where the overhead vapour stream from column A is fully miscible with water, the condensate in the decanter can be suitably split into two portions, one being used as reflux to column A and the other being fed to the upper zone of column B.

From the bottom zone of column A a solution of the hydroxyketone product and the catalyst in the solvent stream containing the water-immiscible solvent and formaldehyde is withdrawn and fed to the middle zone of column B for liquid-liquid extraction of the product into an aqueous phase.

In operating column A, it may be desirable from time to time to remove a vaporous bleed of the water-immiscible solvent and formaldehyde from the bottom zone and feed this vapour into a third column in order to separate the two components by stripping so that a substantially pure stream of the solvent is recovered from the base of this third column and used as the feed or as part of the solvent stream feed to the bottom of column B. The overhead from this third column comprising formaldehyde and solvents can be recycled to the middle zone of column A.

The temperature profile in this column A is suitably in the range from 90° to 150° C. at the base of the column, irrespective of column pressure, and from 75° to 110° C. at the top of column A at ambient pressures.

Column A is adapted to perform several functions. For instance, in this column:

a) Provision is made for continuous water-removal overhead because the presence of water in the reaction system is known to deactivate the catalyst for the process. Thus water and the water-immiscible solvent stream which may comprise a mixture of a relatively low boiling alcohol e.g. iso-butanol, and a relatively high boiling alcohol such as e.g. 4-methylpentan-2-ol, pass from the head of the column and are condensed before passing into a decanter where they form two separate layers. The top layer, containing the majority of the isobutanol is returned to the column. The bottom layer, which is predominantly water, is pumped into column B.

b) The isobutanol performs two important functions. In addition to azeotroping the water from the column, the isobutanol performs another equally important role by providing a means of containing the formaldehyde reactant within the column. The chemical properties of isobutanol are such that it can react to bind free formaldehyde to form a hemiformal which hemiformal has a higher boiling point than pure isobutanol. Therefore, the hemiformal and formaldehyde can be substantially contained within the column. This improves the efficiency of the process.

c) The relatively higher boiling 4-methylpentan-2-ol in the water-immiscible solvent is the less water-miscible reaction solvent of the two alcohols and due to its condensation temperature of 110°–130° C., it remains in the lower regions of column A.

d) Since DHA and the catalyst are relatively involatile, it will be possible to condense and recover as bleed from column A an alcohol stream free of these latter components using this system and this stream can be further purified in a third column to recover as a base stream thereof a substantially pure relatively high boiling alcohol for recycle to column B as feed to that column.

Typically, on a laboratory scale, this column A is a vacuum jacketed glass column of 80 mm diameter fitted with Oldershaw plates and is operated at a pressure of 450–600 mmHg and a reboiler temperature of 110°–130° C. The process can be, however, scaled-up for operations on a commercial scale.

Similarly, column B, where the hydroxyketone product from column A is extracted suitably by liquid-liquid extraction, preferably has from 5 to 20 theoretical stages. The middle zone of this 20 stage column can be defined by the region between theoretical stages 5 and 15. The bottom zone of this column can be defined by a region below theoretical stage 5 and the upper zone of this column can be defined by a region above theoretical stage 15.

As explained previously, the solution of the hydroxyketone product and the catalyst, which may be partially deactivated due to contact with water, in the solvent stream comprising the water-immiscible solvent and possibly formaldehyde, is fed to the middle zone of a 20-stage column B at about theoretical stage 10. Into the base of this column B is fed, in a counter-current mode the substantially pure stream of the water-immiscible solvent optionally recovered from the base of the third column. At the same time, formalin is fed into the upper zone of column B preferably at the top of this column B. The water component of the formalin feed and that of the aqueous phase from the decanter fed at about theoretical stage 15 into the upper zone of column B enable the hydroxyketone product to be extracted into an aqueous stream gravitating to the bottom of column B from where an aqueous solution of the hydroxyketone product together with any traces of impurities such as methanol is withdrawn for use as such or for further purification, concentration or removal of water. In this column B, due to the presence of water from various sources such as e.g. the formalin feed, the catalyst fed to column B from column A may be deactivated.

However, a significant feature of the present invention is that any such deactivation is reversed and the catalyst regenerated under the conditions used in column A. In particular, column A is operated in such a manner that the base of the column, i.e. the kettle, is maintained substantially anhydrous (i.e. it has no more than 0.4%, preferably no more than 0.1% w/w of water) and the upper zone of column A is suitably maintained under such conditions that the overhead vapour stream withdrawn therefrom (which may be an azeotrope) comprises at least a portion of the solvents from the solvent stream, formaldehyde and water.

Column B is operated in such a manner that a stream which comprises the catalyst, formaldehyde and the solvent stream inclusive of the water-immiscible solvent is withdrawn from the upper zone of column B at the top and is fed to the middle zone of column A. The proportion of the various components in this stream can vary widely. As will be apparent to those skilled in the art, it is not necessary to use column B in the conventional sense of a liquid-liquid extraction column. The same objective as defined herein for B can be achieved and performed by using a series of mixer-settlers.

As in the case of column A, column B is multifunctional. In this column there is preferably a continuous aqueous phase and:
a) formaldehyde is extracted from formalin into the organic solvent stream phase rising up the column thereby dramatically reducing the water loading on column A,
b) DHA formed in column A and carried as a solution thereof in the organic solvent stream to be fed to and rising upwards in column B, is extracted (by the water in the continuous aqueous phase flowing down the column B) into an aqueous phase from the organic phase and is recovered from the base of column B, and
c) in the bottom zone, the catalyst and the aldehyde are back-extracted into the organic solvent stream phase from an aqueous solution thereof.

As can be seen from the above and an illustrated description of the process train below substantially all of the reactants and products with the exception of water are recycled or reused in the process and there is little or no loss of any of the chemical components, especially the catalyst which is recycled and reactivated in situ. Thus the process not only is economically very attractive but is also environmentally very desirable as substantially none of the chemical components are discharged into the waste streams from the process.

Clearly, after several recycles, the catalyst may get irreversibly deactivated due to side reactions and consequent undesirable by-products. It may therefore be necessary to remove a bleed somewhere in the process train, preferably from a feed to column A to prevent the build-up of by-products in the system, and to replenish reactants and feed components such as e.g. the catalyst to column A.

More specifically, the process of the present invention is illustrated by the accompanying diagram for the self-condensation of formaldehyde to DHA using a mixture of 4-methypentan-2-ol and isobutanol (50/50) as the water-immiscible components of feed line stream (2).

In the diagram, Column A is the self-condensation reactor with a kettle E, Column B is the liquid-liquid extractor and Column C is the stripping column with a kettle F for recovery of substantially pure water-immiscible solvent to be fed back to Column B.

Line (1) is a feed to the Column B and is an aqueous formalin solution (e.g. 40% w/w) which contains small amounts of methanol and formic acid as impurities.

Line (2) is the water-immiscible solvent/formaldehyde/recycled catalyst stream emerging from Column B and which is fed to Column A as the reactant mixture.

Line (3) is a solution of the hydroxyketone product emerging from the base of Column A and which contains in addition formaldehyde, the catalyst and the water-immiscible solvent and which is used as feed to Column B.

Line (4) is the purified water-immiscible solvent stream (containing traces of the condensation catalyst and formaldehyde) recovered from the base of Column C in which a vaporous bleed (10) of the water-immiscible solvent and formaldehyde is purified. The purified solvent stream is fed to Column B.

Line (5) is a substantially pure aqueous solution of the hydroxyketone product which can be dried or used as such in further reactions as desired.

Line (6) is a vapour stream withdrawn overhead from Column A and after condensation is fed to a decanter D to allow phase separation, if any water-immiscible solvent is present in the overhead vapours. Line (6) usually contains the water-immiscible solvent, water and some formaldehyde.

Line (7) is an aqueous layer recovered from decanter D and contains a small proportion of the water-immiscible solvent, some formaldehyde and water.

Line (8) is either the organic phase containing a high proportion of the water-immiscible alcohol, some water and some formaldehyde, or, in the absence of any water-immiscible solvent, simply a portion of the aqueous solution of formaldehyde and any other water soluble components which is recovered from decanter D and is recycled back to Column A.

Line (9) is the overheads from Column C where the bleed line (10) is purified and this overhead contains a mixture of the water-immiscible solvent and substantially all of the formaldehyde fed to column C via line (10) which is recycled back to Column A.

Line (10) as explained previously is the bleed from Column A which contains the water-immiscible solvent and formaldehyde. The preferred ranges for the composition, temperature and relative flows of the principal streams of the process are given below:

Line 1:
Composition: 10–55% w/w formaldehyde
0–10% w/w methanol
<0.05% w/w formic acid
balance water
Relative flow: 1 (the feed stream used as basis of all the other streams)

Line 2:
Composition: 5–25% w/w formaldehyde, most preferably 10–20%
0.05–3% w/w condensation catalyst, most preferably
1–3% w/w
0.1–16% w/w water

| | |
|---|---|
| | Balance to 100% is water-immiscible alcohol(s). |
| Relative flow: | 2 to 10, most preferably 2.5–4 |
| Line 3: | |
| Composition: | 5–25% w/w hydroxyketone, most preferably 8–15% w/w |
| | 0–15% w/w formaldehyde, most preferably 2–8% w/w |
| | 0.05–3% w/w condensation catalyst, most preferably |
| | 1–3% w/w |
| | Balance to 100% water-immiscible alcohol(s) |
| Temperature: | 40–80° C. |
| Relative flow: | 1–9, most preferably 1.5–3 |
| Line 4: | |
| Composition: | >99% w/w water-immiscible alcohol(s) |
| | <0.005% condensation catalyst |
| | <0.1% formaldehyde |
| Temperature: | 20–150° C., most preferably 40–100° C. |
| Relative flow: | 1.0–9, most preferably 1.0–2 |
| Line 5: | |
| Composition: | 5–55% w/w hydroxyketone, most preferably 25–40% w/w |
| | Balance to 100% water |
| Temperature: | 20–80° C., preferably 30–50° C. |
| Relative flow: | 1 |

It will be appreciated that other configurations are possible to produce the backwash stream, line 4. One approach would be to take the bleed stream (line 10) from the organic phase in the decanter, D rather than from the lower region of column A. This can then be made free of formaldehyde so as to meet the composition of line 4 by various means.

One method is to feed it to the midpoint of column C, and to operate this column at a suitable vacuum such that the heads product is substantially free of formaldehyde, the condensed heads stream then providing the backwash, line 4. This requires a substantial number of plates, typically between 25 and 80 being used.

Another method of removing formaldehyde from the decanter organic phase is to transform it by chemical reaction to a material which is acceptable in the alpha-hydroxyketone product. For many purposes, hydrogenation of the stream over a heterogeneous catalyst is suitable, thus converting the formaldehyde to methanol which is already present as a minor constituent of the product stream, line 5.

Other chemical treatments such as oxidation could also be applied depending on the downstream application of the hydroxyketone product.

The process of the present invention is particularly applicable to the production of dihydroxyacetone in good yields and high purity in that the product is not contaminated to any significant extent with any species which may adversely affect any catalytic reactions to which the hydroxyketone may be subjected such as e.g. the hydrogenation thereof to glycerol.

It will be apparent to those skilled in the art that the process of the present invention can be equally applied to produce predominantly erythrulose.

We claim:

1. A continuous process for producing hydroxyketones by condensation of one or more aldehydes in the presence of a catalyst derived from a thiazolium or imidazolium salt characterised in that the process is carried out in a process train comprising at least two columns A and B such that:
   1.1 column A is the condensation reactor which is provided with notional zones comprising:
      a. a middle zone into which is fed a feed comprising the aldehyde(s), a solvent stream comprising at least one water-immiscible organic solvent, and a catalyst;
      b. a bottom zone in which a condensation of the aldehyde(s) occurs under substantially anhydrous conditions and from which a solution comprising the hydroxyketone, catalyst and the solvent stream is withdrawn for extraction of the hydroxyketone product therefrom in column B; and
      c. an upper zone from which a mixture comprising unreacted aldehyde(s), whether as such or in bound form, one or more components of the solvent stream, whether or not water-miscible, and water are withdrawn; and
   1.2 column B is an extraction column which is provided with three notional zones comprising:
      a. a middle zone into which is fed the solution comprising the hydroxyketone, the catalyst and the solvent stream withdrawn from the bottom of column A;
      b. a bottom zone
         (i) into which is fed a solvent stream comprising the water-immiscible organic solvent and
         (ii) from which an aqueous solution of the hydroxyketone product is withdrawn; and
      c. an upper zone
         (i) into which is fed an aqueous solution of the aldehyde(s) and
         (ii) from which a feed comprising the solvent stream, the aldehyde(s), whether as such or in bound form, and catalyst is withdrawn for recycle to the middle zone of column A, thereby enabling in column B a simultaneous recovery of the hydroxyketone product and recycle of the catalyst to column A.

2. A process according to claim 1 wherein the hydroxyketone is produced by the self-condensation of an aldehyde.

3. A process according to claim 2 wherein dihydroxyacetone is produced by self-condensation of formaldehyde.

4. A process according to claim 3 wherein the formaldehyde used is formalin comprising 30–60% w/w of formaldehyde.

5. A process according to claim 1 wherein the water-immiscible component of the solvent stream is selected from a hydrocarbon, a halohydrocarbon, an ether, an ester and an alcohol.

6. A process according to claim 5 wherein the water-immiscible component of the solvent stream is an aliphatic alcohol selected from secondary butanol, and isobutanol, iso-amyl alcohol, active amyl alcohols and 4-methylpentan-2-ol.

7. A process according to claim 1 wherein the condensation catalyst is derived from a thiazolium salt or an imidazolium salt of an anion $X^-$ by abstraction of the compound $H^+X^-$ therefrom.

8. A process according to claim 7 wherein the condensation catalyst is derived from an alkyl benzothiazolium halide.

9. A process according to claim 1 wherein column A has 10 to 40 theoretical plates such that the notional middle zone of the column is in a region between plates 15 and 30, the notional bottom zone is in a region below theoretical plate 15 and the notional upper zone is in a region above theoretical plate 30.

10. A process according to claim 1 wherein the temperature profile in column A is such that it is in the range of 90°–150° C. at the base of the column and 75°–110° C. at the top of the column at ambient pressures.

11. A process according to claim 1 wherein column B has from 5–20 theoretical stages, such that the notional middle zone is in a region between stages 5 and 15, the notional bottom zone is in a region below stage 5 and the notional upper zone is in a region above stage 15.

12. A process according to claim 1 wherein column A is operated in such a manner that the base of the column is maintained substantially anhydrous and the overhead vapour stream withdrawn from the upper zone of the column comprises at least a portion of the solvents from the solvent stream, formaldehyde and water.

13. A process according to claim 1 wherein column B is operated in such a manner that a stream comprising the catalyst, formaldehyde and the solvent stream inclusive of the water-immiscible solvent is withdrawn from the upper zone at the top of the column and fed to the middle zone of column A.

14. A process according to claim 1 wherein the hydroxyketone formed in column A and withdrawn from the bottom zone thereof as a solution in an organic solvent stream is fed to and rising upwards in column B wherefrom the hydroxyketone is extracted into an aqueous phase flowing downwards in column B in counter-current fashion with respect to the organic solvent solution of the hydroxyketone feed to column B.

15. A process according to claim 1 wherein the functions of column B are performed by a series of mixer-settlers.

* * * * *